United States Patent

Schut et al.

[11] 4,232,160
[45] Nov. 4, 1980

[54] ISOQUINOLINE PROPIONAMIDES EXHIBITING ANALGESIC PROPERTIES

[75] Inventors: Robert N. Schut, Edwardsburg, Mich.; Edgar O. Snoke; John W. Van Dyke, Jr., both of Elkhart, Ind.

[73] Assignee: Miles Laboratories, Inc., Elkhart, Ind.

[21] Appl. No.: 952,212

[22] Filed: Oct. 18, 1978

[51] Int. Cl.³ .................. C07D 217/16; A61K 31/47
[52] U.S. Cl. .................................... 546/146; 424/258
[58] Field of Search ................ 546/147, 146; 424/258

[56] References Cited

U.S. PATENT DOCUMENTS

| 3,389,140 | 6/1968 | Montzka | 546/146 |
| 3,557,120 | 1/1971 | Archer et al. | 546/147 X |
| 3,985,881 | 10/1976 | Mehrhof et al. | 424/258 |

*Primary Examiner*—Donald G. Daus
*Assistant Examiner*—Diana G. Rivers
*Attorney, Agent, or Firm*—Jerome L. Jeffers

[57] ABSTRACT

Disclosed are novel isoquinoline propionamides and their acid salts represented by the structural formula:

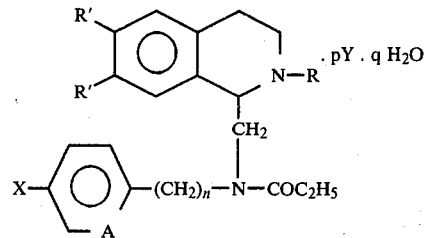

wherein R is alkyl of 1 to 6 carbon atoms, methylcycloalkyl of 4 to 7 carbon atoms or alkaryl of 7 to 8 carbon atoms;
R' is H or OCH₃;
A is N or CH;
X is H, Cl or CH₃;
n is 0 or 1;
Y is a pharmacologically acceptable, non-toxic acid and p and q are 0 or 1. These compounds exhibit analgesic properties.

2 Claims, No Drawings

_4,232,160_

ISOQUINOLINE PROPIONAMIDES EXHIBITING ANALGESIC PROPERTIES

BACKGROUND OF THE INVENTION

1. Field of the Invention

This invention involves isoquinoline propionamides and a method for their preparation. The novel compounds of this invention have been found to exhibit potent analgesic activity in in vivo tests.

2. Prior Art

U.S. Pat. No. 3,389,140 discloses isoquinoline type compounds of the formula:

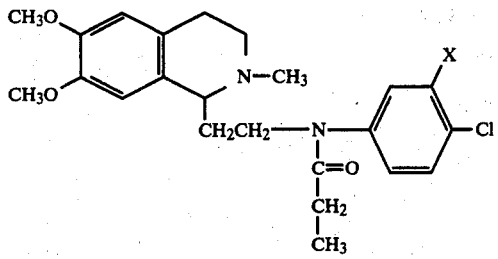

wherein X is hydrogen or chlorine which are said to be useful as analgesics.

Compounds of the general formula:

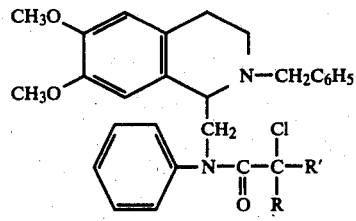

where R and R' can be hydrogen or methyl are disclosed in U.S. Pat. No. 3,557,120 as being useful intermediates in the preparation of hexahydroimidazoisoquinalines having utility as sedatives.

SUMMARY OF THE INVENTION

The present invention is concerned with isoquinoline propionamides and pharmacologically acceptable, non-toxic acid addition salts thereof. These compounds are represented by the formula:

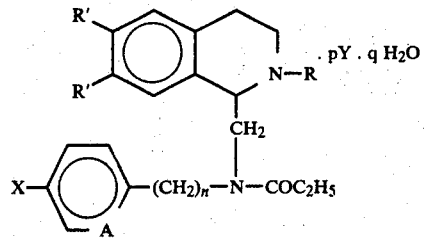

In the above formula R is alkyl of 1 to 6 carbon atoms, methylcycloalkyl of 4 to 7 carbon atoms or alkaryl of 7 to 8 carbon atoms;
R' is H or $OCH_3$;
A is N or CH;
X is H, Cl or $CH_3$;
n is 0 or 1;
Y is a pharmacologically acceptable, non-toxic acid and p and q are 0 or 1.

DETAILED DESCRIPTION OF THE INVENTION

The compounds of the instant invention, represented by Formula I,

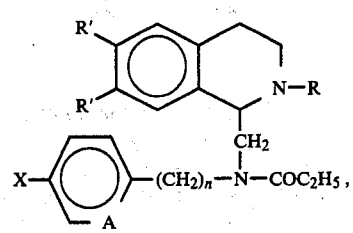

wherein R, R', X, A and n are as defined above, can be prepared by one of two methods, which are:

A. By first preparing the diamine II

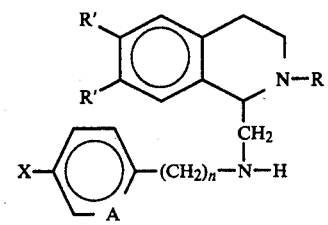

and then treating it with either propionyl chloride or propanoic anhydride in the presence of sodium bicarbonate. The preparation of the diamine and its conversion to the corresponding propionamide is represented in Scheme A.

SCHEME A

The diamine is prepared from the N-phenyl or pyridinylisoquinaldamide III prepared by either the method disclosed in _J. Org. Chem._, 26, 1161 (1961) or that disclosed in U.S. Pat. No. 3,557,120. The N-phenyl or pyridinylisoquinaldamide III is catalytically reduced and then alkylated to give intermediate IV by the following reaction sequence in which R, R', X, A and n are as defined above where n=0.

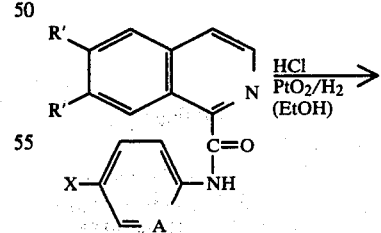

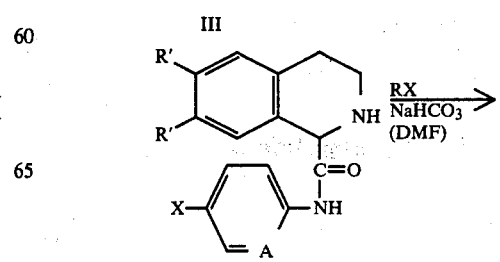

-continued

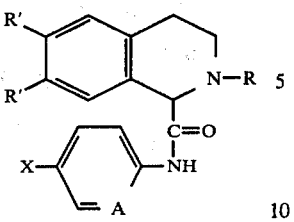
IV

The N-methyl compound, i.e. compound IV where R=CH₃, is more readily prepared by first making the quaternary salt of III with MeI and then catalytically reducing it to IV where R=CH₃ by the following reaction sequence:

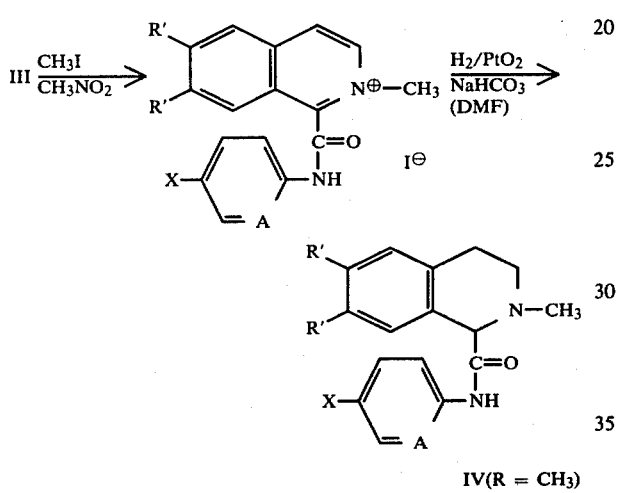
IV(R = CH₃)

Compound IV is then reduced chemically (Li AlH₄) to the corresponding diamine V (n=0).

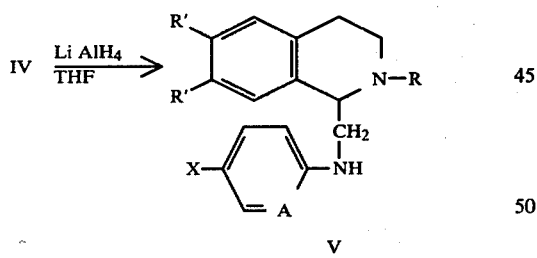
V

An alternative method for the preparation of V where R is a group other than H is to prepare IV where R is H and then alkylating in the final step.

Preparation of the diamine where n=1 is accomplished by chemically reducing the appropriate 2-substituted-1,2,3,4-tetrahydroisoquinoline-1-carboxamide VI to the primary amine VII.

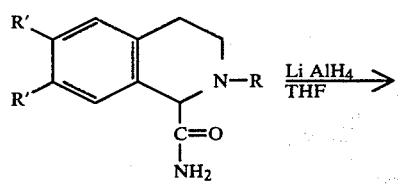
VI

-continued

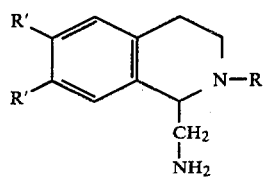
VII

The primary amine where R is methyl can also be prepared from 1-cyanoisoquinoline by a series of reactions including catalytic reduction, protecting the amine formed as the amide, quaternization, reduction to the tetrahydro compound and hydrolysis of the amide as represented by the following reaction scheme:

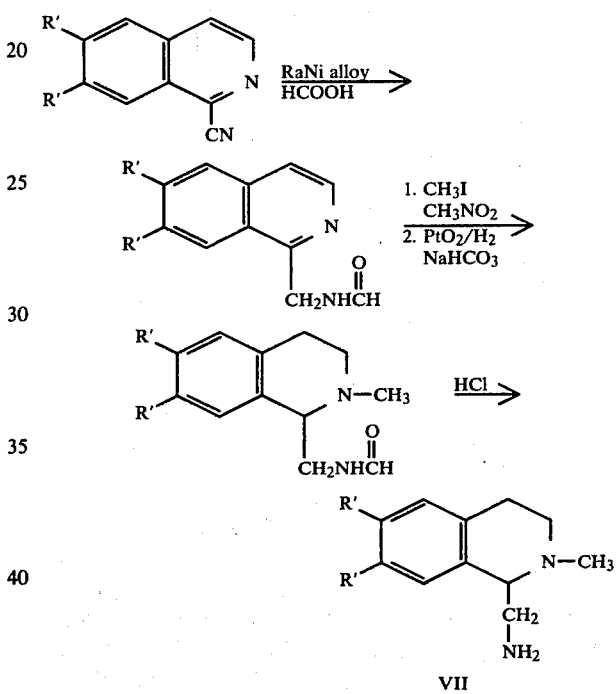
VII

The primary amine VII is then reacted with substituted or unsubstituted benzaldehyde, XC₆H₄CHO, or pyridine carboxaldehyde, XC₅NH₃CHO to form the Schiff base which is reduced chemically with NaBH₄ to form the secondary diamine VIII (n=1).

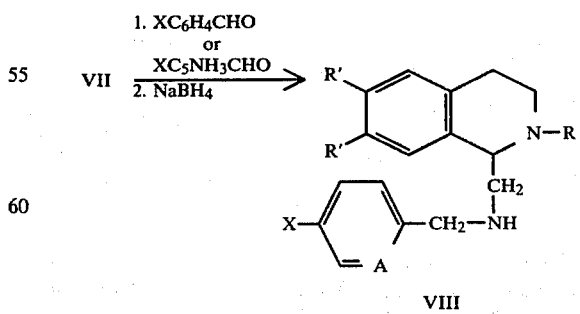
VIII

The diamine V (n=0) or VIII (n=1) is then propionylated using either propanoic anhydride or propionyl chloride to form the title Compound I.

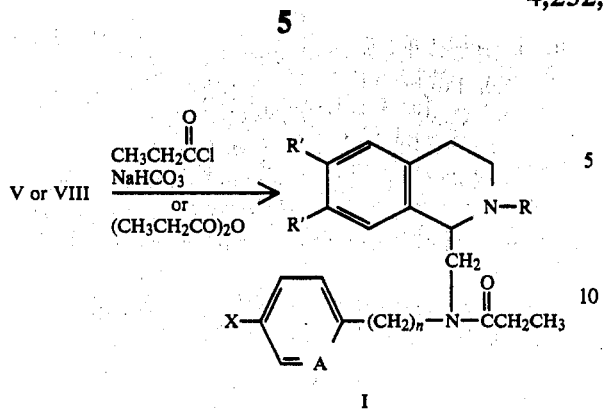

B. By first preparing the propionamide IX:

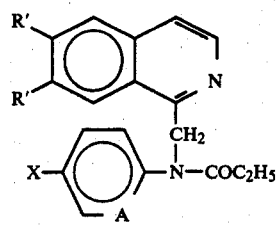

and then making the quaternary salt and reducing the isoquinoline ring. Method B is set out in Scheme B.

SCHEME B

The 1-methyl isoquinoline or 6,7-dimethoxy-1-methylisoquinoline is oxidized with $SeO_2$ to the corresponding aldehyde which is reacted with aniline or 4 chloro or 4 methyl aniline to form the Schiff based which is reduced chemically to form the anilino compound which is propionylated to yield IX as indicated by the following reaction sequence:

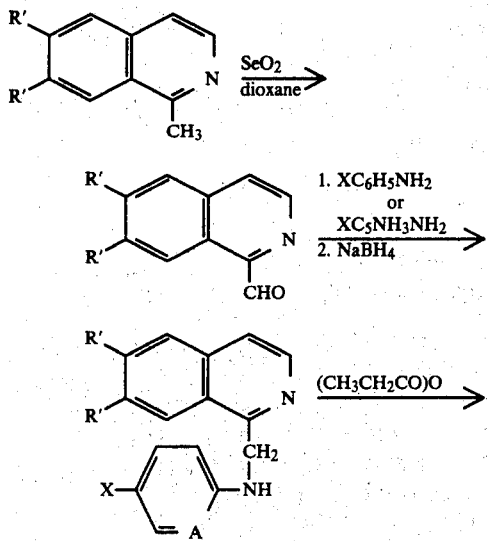

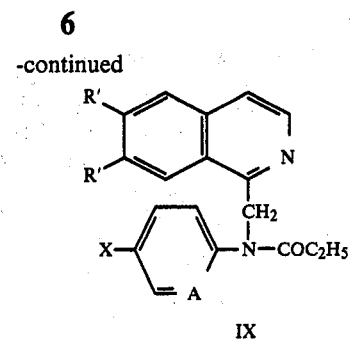

Compound IX can be quaternized and then catalytically reduced to the title Compound I where n=0.

The method of practicing the invention is further illustrated by the following examples in which all temperatures are in °C.

EXAMPLE I

Preparation of
N-[(1,2,3,4-Tetrahydro-2-methyl-1-isoquinolyl)methyl]-propionanilide hydrochloride (TR-3284)

Title Compound I, in which R=CH₃; R'=H, A=CH; pY=HCl and q and n=0, was prepared by first refluxing 5.0 g. (0.02 mole) of N-phenylisoquinaldamide with 30 ml. of methyl iodide for 48 hours. The excess methyl iodide was distilled and the resulting brown solution cooled to yield 4.66 g. (60% of theory) of the methiodide (melting range 204°-5° from nitromethane).

Anal. Calcd. for $C_{17}H_{18}IN_2O$: C, 52.32; H, 3.87; N, 7.18. Found: C, 52.39; H, 3.88; N, 7.00.

The methiodide was shaken in a Paar apparatus initially at 60 psi of hydrogen for 2 hours with 0.3 g. of $PtO_2$ in 150 ml. of $CH_3OH$ whereupon the catalyst was removed by filtration and the filtrate concentrated and neutralized with saturated, aqueous $NaHCO_3$. The aqueous residue was extracted with $CHCl_3$, the organic layer separated, dried over $MgSO_4$ and evaporated in vacuo to yield 2.6 g. (70% theory) of 1-phenylcarbamoyl-2-methyl-1,2,3,4-tetrahydroisoquinoline (IV,X=H) as a tan solid (m.p. 80°-80.5° from 95% ethanol).

Anal. Calcd. for $C_{12}H_{18}N_2O_2$: C, 76.67; H, 6.81; N, 10.52. Found: C, 76.25; H, 6.76; N, 10.43.

To a stirring suspension of lithium aluminum hydride (2.5 g. in 100 ml. anhydrous THF) was added dropwise a solution of 6 g. (0.023 mole) of the material prepared immediately above in 35 ml. anhydrous THF. The reaction was refluxed for 15 hours and treated with 30 ml. of a 1:2 water:THF solution. Dichloromethane (100 ml.) was added and the solids removed by filtration. The filtrate was dried with MgSO$_4$ and evaporated in vacuo to leave a yellow oil (4.3 g). The oil was dissolved in hot 2-propanol with an equimolar amount of oxalic acid and allowed to cool. After two further recrystallizations from 2-propanol, 1.0 g (13% theory) of 1-(N-phenyl-)aminomethyl-2-methyl-1,2,3,4-tetrahydroisoquinoline oxalate was obtained.

Anal. Calcd. for $C_{17}H_{20}N_2 \cdot C_2H_2O_4$: C, 66.66; H, 6.48; N, 8.18. Found: C, 67.15; H, 6.54; N, 8.17.

The oxalate of VI (R=CH$_3$; the free base can also be used) was stirred in a mixture of 25 ml. CH$_2$Cl$_2$ and 25 ml. saturated NaHCO$_3$ solution. In this step 3.0 g (0.0088 mole) of the oxalate was used. Propionyl chloride (0.92 g–0.01 mole) was added slowly and the stirring allowed to continue for an additional hour whereupon the organic layer was separated, dried with MgSO$_4$ and evaporated in vacuo to leave 2.63 g of a brown oil. The free base was dissolved in ether, treated with charcoal, filtered and the filtrate treated with 2-propanolic hydrogen chloride dropwise to precipitate the hydrochloride salt which was recrystallized from ethyl acetate/2-propanol (ca 10:1) to yield 2.27 g. of a white solid m.p. 173.5°–175° C.

Anal. Calcd. for $C_{20}H_{24}N_2O \cdot HCl$: C, 69.64; H, 7.30; N, 8.12. Found: C, 68.39; H, 7.51; N, 7.96.

EXAMPLE II

Preparation of N-[(1,2,3,4-Tetrahydro-2-cyclopropylmethyl-1-isoquinolyl)methyl]propionanilide hydrochloride (TR-3207)

Title Compound I, in which R=CH$_2$C$_3$H$_5$; R'=H; X=H; A=CH; pY=HCl and n and q=0 was prepared by first dissolving N-phenylisoquinaldamide (6 g; 0.024 mole) in 200 ml. of absolute ethanol with heating. The solution was placed in a Paar pressure bottle and 2 g concentrated hydrochloric acid added whereupon a thick yellow precipitate formed. At this point PtO$_2$ (200 mg.) was added and the mixture reduced in a Paar hydrogenator initially set at 55 psi. After 2½ hours the reaction was stopped and the catalyst removed by filtration. The filtrate was evaporated almost to dryness in vacuo and neutralized with a saturated NaHCO$_3$ solution. The resulting mixture was extracted with CHCl$_3$, the organic layer dried over MgSO$_4$ and evaporated in vacuo leaving 6.0 g of an oil. Trituration with 95% ethanol yielded 4 g (66%) N-phenyl-1,2,3,4-tetrahydroisoquinaldamide (white solid, m.p. 133°–5° from ethanol). This solid (2.52 g; 0.01 mole) was refluxed with stirring for 2 hours in 25 ml. dimethylformamide (DMF) with 1.5 g (0.011 mole) cyclopropylmethyl bromide and 1.0 g (0.012 mole) of NaHCO$_3$. The DMF was removed by heating in vacuo and the residue suspended between water and CHCl$_3$ at which point the organic layer was separated, dried over MgSO$_4$ and evaporated in vacuo leaving a reddish oil. The oil was dissolved in a small amount of HCl/2-propanol and poured into 200 ml. absolute ether. After standing for several hours, 1.7 g (50% theory) of 1-phenylcarbamoyl-1,2,3,4-tetrahydroisoquinoline.HCl (pale pink solid, melting range 227°–9°) was obtained.

Anal. Calcd. for $C_{20}H_{22}N_2O \cdot HCl$: C, 70.05; H, 6.76; N, 8.7. Found: C, 69.43; H, 6.70; N, 8.35.

The amide was reduced with LiAlH$_4$ as in Example I to provide 1-(N-phenyl)Aminomethyl-2-cyclopropylmethyl-1,2,3,4-tetrahydroisoquinoline oxalate which was found to have a melting range of 157°–9°.

Anal. Calcd. for $C_{20}H_{24}N_2 \cdot C_2H_2O_4$: C, 69.13; H, 6.85; N, 7.32. Found: C, 69.06; H, 6.97; N, 7.28.

The acylation procedure used in Example I was used to provide N-[(1,2,3,4-Tetrahydro-2-cyclopropylmethyl-1-isoquinolyl)methyl]propionanilide hydrochloride (m.p. 136°).

Anal. Calcd. for $C_{23}H_{27}N_2O \cdot HCl$: C, 71.93; H, 7.35; N, 7.30. Found: C, 71.05; H, 7.67; N, 7.37.

EXAMPLE III

Preparation of N-[(1,2,3,4-Tetrahydro-2-n-hexyl-1-isoquinolyl)methyl]propionanilide oxalate hydrate (TR-3309)

Title Compound I, in which R=(CH$_2$)$_5$CH$_3$; R'=H; X=H; A=CH; pY=C$_2$H$_2$O$_4$; q=1 and n=0, was prepared as in Example II using n-hexylbromide instead of cyclopropylmethylbromide. The compound was found to have a melting point of 96°.

Anal. Calcd. for $C_{25}H_{34}N_2O \cdot C_2H_2O_4 \cdot H_2O$: C, 66.66; H, 7.87; N, 5.75. Found: C, 67.58; H, 7.96; N, 5.83.

EXAMPLE IV

Preparation of N-[(1,2,3,4-Tetrahydro-2-n-pentyl-1-isoquinolyl)methyl]propionanilide hydrochloride (TR-3316)

Title Compound I, in which R=(CH$_2$)$_4$CH$_3$; R'=H; A=CH; pY=HCl and q and n=0 was prepared as in Example II using n-pentylbromide instead of cyclopropylmethylbromide. The compound was found to have a melting range of 108°–111°.

Anal. Calcd. for $C_{24}H_{32}N_2O \cdot HCl$; C, 71.88; H, 8.30; N, 6.99. Found: C, 71.60; H, 8.66; N, 6.84.

EXAMPLE V

Preparation of N-[(1,2,3,4-Tetrahydro-2-phenethyl-1-isoquinolyl)methyl]propionanilide hydrochloride (TR-3280)

Title Compound I, in which R=CH$_2$CH$_2$C$_6$H$_5$; R'=H; X=H; A=CH; pY=HCl and q and n=0 was prepared as in Example II using phenethylbromide instead of cyclopropylmethylbromide. The compound was found to have a melting range of 155°–6°.

Anal. Calcd. for $C_{27}H_{30}N_2O \cdot HCl$; C, 74.54; H, 7.18; N, 6.44. Found: C, 74.98; H, 7.29; N, 6.52.

EXAMPLE VI

Preparation of N-[(1,2,3,4-Tetrahydro-2-i-pentyl-1-isoquinolyl)methyl]propionanilide hydrochloride (TR-3317)

Title Compound I, in which R=CH$_2$CH$_2$CH(CH$_3$)$_2$; R'=H; X=H; A=CH; pY=HCl and q and n=0 was prepared as in Example II using isopentylbromide instead of cyclopropylmethylbromide. The compound was found to have a melting range of 144°–5°.

Anal. Calcd. for $C_{24}H_{32}N_2O \cdot HCl$: C, 71.88; H, 8.30; N, 6.99. Found: C, 71.41; H, 8.54; N, 6.72.

EXAMPLE VII

Preparation of
N-[(1,2,3,4-Tetrahydro-2-methyl-1-isoquinolyl)methyl]N-(4-chlorophenyl)propionamide hydrochloride (TR-3354)

Title Compound I, in which R=CH$_3$; R'=H; X=Cl; A=CH; pY=HCl and q and n=0 was prepared as in Example I with N-4-chlorophenylisoquinaldamide as the starting material. The compound was found to have a melting range of from 215°–217°.

Anal. Calcd. for C$_{20}$H$_{23}$ClN$_2$O.HCl: C, 63.31; H, 6.38; N, 7.38. Found: C, 64.29; H, 6.39; N, 7.22.

EXAMPLE VIII

Preparation of
N-[(1,2,3,4-Tetrahydro-2-methyl-1-isoquinolyl)methyl]-N-(4-methylphenyl)propionamide hydrochloride (TR-3355)

Title Compound I in which R=CH$_3$; R'=H; X=CH$_3$; A=CH; pY=HCl and q and n=0 was prepared as in Example I starting with N-4-methylphenylisoquinaldamide and found to have a melting range of 202°–3°.

Anal. Calcd. for C$_{21}$H$_{26}$N$_2$O.HCl: C, 70.27; H, 7.58; N, 7.81. Found: C, 69.41; H, 7.58; N, 7.54.

EXAMPLE IX

Preparation of
N-[(1,2,3,4-Tetrahydro-2-benzyl-1-isoquinolyl)methyl]-propionanilide hydrochloride (TR-3359)

Title Compound I, in which R=CH$_2$C$_6$H$_5$; R=H; X=H; A=CH; pY=HCl and q and n=0, was prepared as in Example II using benzylbromide instead of cyclopropylmethyl bromide. The compound was found to have a melting range of 190°–193°.

Anal. Calcd. for C$_{26}$H$_{28}$N$_2$O.HCl: C, 74.17; H, 6.94; N, 6.65. Found: C, 73.79; H, 6.83; N, 6.42.

EXAMPLE X

Preparation of
N-[(1,2,3,4-Tetrahydro-2-methyl-1-isoquinolyl)methyl]-N-benzylpropionamide oxalate (TR-3389)

Title Compound I, in which R=CH$_3$ R'=H; X=H; A=CH; pY=C$_2$H$_2$O$_4$ and q=0 and n=1 was prepared as follows:

1-Cyanoisoquinoline (15.4 g; 0.1 mole) was stirred and heated at reflux for 2.5 hours in 900 ml. of a 1:1 formic acid water solution with 30 g of Raney nickel alloy. The reaction was filtered and the filtrate made basic with 20% NaOH. The resulting suspension was extracted with dichloromethane whereupon the organic layer was separated, dried over MgSO$_4$ and evaporated in vacuo to leave 9.5 g of a green oil. The crude oil was chromatographed through a silica gel column with ethyl acetate; evaporation of the ethyl acetate in vacuo left 7.5 g (40% theory) of 1-formamidoisoquinoline as a yellow oil. This compound was converted to the methiodide salt and reduced catalytically as in Example I to give a 50% yield of 1-formamidomethyl-2-methyl-1,2,3,4-tetrahydroisoquinoline as a yellow oil, 4 g (0.02 mole) of which was refluxed for 60 minutes in 10 ml of concentrated HCl. The acid solution was made basic with 20% NaOH and concentrated in vacuo. The residue was extracted with CHCl$_3$, the organic layer dried over MgSO$_4$ and evaporated in vacuo to leave 2.7 g (69%) of 1-aminomethyl-2-methyl-1,2,3,4-tetrahydroisoquinoline as an oil. The 2.7 g (0.015 mole) of the above and 1.6 g (0.015 mole) of benzaldehyde were heated to reflux in 30 ml benzene to which a catalytic amount of p-toluenesulfonic acid had been added. After refluxing for 15 hours the benzene was evaporated in vacuo leaving a reddish residue. The residue was stirred at 0° in 30 ml of absolute methanol whereupon NaBH$_4$ (5 g) was added slowly. After 45 minutes the reaction mass was allowed to come to room temperature and then allowed to stir for 10 minutes more. The methanol was removed in vacuo and the residue suspended between water and dichloromethane. At this point the organic layer was separated, dried over MgSO$_4$ and the solvent removed in vacuo to yield 3.8 g (93% theory) of 1-(N-benzyl)aminomethyl-2-methyl-1,2,3,4-tetrahydroisoquinoline as an oil. The oil was propionylated as in Example I and the oxalate (having a melting range of 136°–7°) was formed.

Anal. Calcd. for C$_{21}$H$_{26}$N$_2$O.C$_2$H$_2$O$_4$: C, 66.97; H, 6.84; N, 6.79. Found: C, 67.06; H, 6.64; N, 6.59.

EXAMPLE XI

Preparation of
N-[(1,2,3,4-Tetrahydro-2-benzyl-1-isoquinolyl)methyl]-N-benzylpropionamide oxalate (TR-3388)

Title Compound I, in which R=CH$_2$C$_6$H$_5$; R'=H; A=CH; pY=C$_2$H$_2$O$_4$, q=0 and n=1, was prepared by reducing 2-benzyl-1,2,3,4-tetrahydroisoquinoline-1-carboxamide (6.7 g; 0.025 mole) with LiAlH$_4$ by the same procedure as used in Example I to obtain 3.77 g (60% theory) of 1-aminomethyl-2-benzyl-1,2,3,4-tetrahydroisoquinoline as a yellow oil. This compound was reacted with benzaldehyde and reduced as in Example II. The resultant 1-(N-benzyl)aminomethyl-2-benzyl-1,2,3,4-tetrahydroisoquinoline was propionylated as in Example I and the oxalate (having a melting range of 159°–61°) formed.

Anal. Calcd. for C$_{27}$H$_{30}$N$_2$O.C$_2$H$_2$O$_4$: C, 71.29; H, 6.60; N, 5.73. Found: C, 71.81; H, 6.68; N, 5.52.

EXAMPLE XII

Preparation of
N-[(6,7-Dimethoxy-2-methyl-1,2,3,4-tetrahydro-1-isoquinolyl)methyl]propionanilide (TR-3426)

Title Compound I, in which R=CH$_3$; R'=OCH$_3$; X=H; A=CH; and p, q and n=0 was prepared by first refluxing 6,7-dimethoxy-1-methylisoquinoline (11 g; 0.054 mole) in 150 ml. of dry dioxane. To this was added 5.5 g (0.054 mole) SeO$_2$ in 175 ml. of dry dioxane (added 30 ml. portions every 5 minutes) with continued stirring and refluxing for another 3 hours. At the end of this period the reaction was filtered through dicalite. After repeated treatment with charcoal the solution turned clear (medium yellow in color). This was evaporated in vacuo leaving 10.2 g of a sticky brown solid. The solid was dissolved in 95% ethanol and treated with charcoal; the mixture was filtered and allowed to stand and filtered again to yield 5.3 g of 6,7-dimethoxy-1-isoquinolinecarboxaldehyde having a melting range of 177°–8°. The aldehyde (3.25 g) was dissolved in benzene (100 ml.) and aniline (1.4 g) and a catalytic amount of p-toluenesulfonic acid added. The mixture was refluxed for 3 hours using a Dean-Starke trap, the solvent removed in vacuo and the residue suspended in cold methanol (100 ml.). At this point, NaBH$_4$ (3.5 g) was added portionwise in an ice-bath, the mixture allowed to warm to room temperature and then stirred overnight. The solvent was removed in vacuo and the residue treated with $CHCl_3$-$H_2O$ whereupon the $CHCl_3$ layer was dried over $MgSO_4$, filtered and the solvent removed. The material was dissolved in dry benzene (50 ml.) and 5 ml. propionic anhydride added. The reaction was refluxed for 6 hours and cooled to room temperature, the solvent removed in vacuo and the residue treated with aqueous $NaHCO_3$ and then extracted with ether. The ether was dried over $MgSO_4$, filtered and the ether removed in vacuo. The residue (5 g) was recrystallized from ether (Nuchar treatment) and N-[6,7-dimethoxy-1-isoquinolyl)methyl]propionanilide (3.8 g; melting range 129°-30°) was obtained. The yellow solid was heated at reflux for 6 hours with $CH_3I$ (10 ml.) and $CH_3NO_2$ (50 ml.) whereupon the solvent was removed and the residue treated with $NaHCO_3$-$CHCl_3$. The crude solid (5.3 g) was obtained and recrystallized from ethanol/ethyl acetate/ether to yield 4.65 g of the quaternary salt having a melting range of 226°-8°. The quaternary salt was hydrogenated in 100 ml. of 95% ethanol using $PtO_2$. After running the hydrogenation at 50 psi for 3 hours, the catalyst was filtered and washed with 95% ethanol. The solvent was removed and the residue treated with $NaHCO_3$ and extracted with $CHCl_3$ whereupon the $CHCl_3$ was dried and the solvent removed to yield 3.39 g of solid product. The solid was recrystallized twice from Skelly Solve B, a commercially available petroleum ether, to yield 3.0 g of product having a melting range of 100°-102°.

Anal. Calcd. for $C_{22}H_{28}N_2O_3$: C, 71.71; H, 7.66; N, 7.60. Found: C, 72.34; H, 7.90; N, 7.49.

EXAMPLE XIII

Preparation of
N-[(2-Methyl-1,2,3,4-tetrahydro-1-isoquinolyl)methyl]-N-(2-pyridyl)priopionamide hydrochloride (TR-3461)

Title Compound I, in which R=$CH_3$; R'=H; X=H; A=N; pY=HCl and q and n=0 was prepared by first dissolving 1-isoquinolinecarboxaldehyde (6.4 g) and 2-aminopyridine (3.83 g) in 150 ml. of benzene with the addition of a catalytic amount of p-toluenesulfonic acid. The mixture was refluxed overnight using a Dean-Starke trap, the solvent removed in vacuo and the residue treated with $CHCl_3$/$H_2O$. The $CHCl_3$ extract was dried and the solvent removed. The crude Schiff base (9.4 g) was suspended in 150 ml. cold methanol and 10 g of $NaBH_4$ added portionwise in an ice bath. After the addition was complete the ice bath was removed and the mixture stirred at room temperature overnight. An insoluble red solid (2.6 g) was filtered and the methanol concentrated in vacuo. The viscous liquid (6.1 g) was dissolved in benzene (100 ml.) and propionic anhydride (10 ml.) added. The mixture was refluxed for 5 hours and the solvent removed in vacuo. The residue was treated with $CHCl_3$-$NaHCO_3$ solution and the $CHCl_3$ layer dried and concentrated. The residue was washed repeatedly with $H_2O$, the residue taken up in $CHCl_3$, dried and the solvent removed to yield 7 g of a solid. Since N-H absorption was still present in the IR spectrum, the residue was dissolved in $CH_2Cl_2$ (100 ml.) and 4.8 g $NaHCO_3$ in $H_2O$ added. The mixture was stirred vigorously during the addition of 5.4 g propionyl chloride. The stirring was continued for an additional hour, the $CH_2Cl_2$ layer separated and the solvent removed. The residue was stirred with $H_2O$ repeatedly, decanted and taken up in $CH_2Cl_2$ whereupon the layer was dried, filtered and concentrated in vacuo to yield 5.6 g of material. The treatment with propionyl chloride was repeated yielding 5.43 g of material. This material when eluted with ether and $CHCl_3$ was consistant for N-(1-isoquinolyl)methyl-N-(2-pyridyl)propionamide IR analysis—yield 1.7 g. At this point, the amide and $CH_5I$ (0.83 g) were dissolved in 100 ml. of $CH_3NO_2$ and the solution refluxed for 24 hours whereupon the solvent was removed in vacuo. The so-formed quaternary salt (2.4 g) was dissolved in 100 ml. of 95% ethanol and 10% Pd on carbon added. The mixture was hydrogenated at 50 psi with the reaction being complete after 0.5 hours. After 2 hours to ensure complete reduction the mixture was filtered and the filter cake washed with 95% ethanol. The solvent was removed, the residue treated with a $NaHCO_3$ solution whereupon the organic material was extracted with $CHCl_3$, dried over $MgSO_4$ and the solvent removed to yield 1.27 g of product. This material, in the form of a viscous liquid, was chromatographed on a silica gel column and the recovered material (0.78 g) eluted with $CHCl_3$ and ethyl acetate was consistant for N-[2-methyl-1,2,3,4-tetrahydro-1-isoquinoyl]methyl-N-(2-pyridyl)propionamide. The monohydrochloride, which was prepared by adding HCl in 2-propanol and then ethyl actate. The solid formed was recrystallized from 2-propanol/ethyl acetate. The analysis was not correct so the solid was suspended in ether and dry HCL bubbled in. The solid was heated in 2-propanol/ethyl acetate and the filtered solid (150 mg.; m.p. 176°-8°) dried in a 100° C. oven over the weekend.

Anal. Calcd. for $C_{19}H_{23}N_3O.HCl$: C, 65.98; H, 6.99 N, 12.15. Found C, 64.83; H, 6.76; N, 12.23.

EXAMPLE XIV

The analgesic activity of the isoquinoline propionanilides prepared as described in Examples I-XIII was determined by the acetic acid induced writhing test described by Whittle et al., Brit. J. Pharmacol, 22 296 (1964). In this test at least three groups of five male CD-1 mice each were given subcutaneous doses of the test drug dissolved in either distilled water or distilled water acidified with HCl depending on solubility of the compound. In all cases 0.4 ml. of 0.5% v/v acetic acid in distilled water was administered intraperitoneal 15 minutes post drug. The number of writhes in a 20 minute interval beginning 5 minutes after the acetic acid injection were determined and compared with the number of writhes in control groups which had received only acetic acid. In two cases the ITME writhing test protocol was used which is the same as that outlined above except that the number of writhes are determined for 10 minutes after the administration of acetic acid.

Percent inhibition of writhing was calculated as:

$$\% \text{ inhibition} = \left[ \frac{\text{No. Control Writhes} - \text{No. Treated Writhes}}{\text{No. Control Writhes}} \right]$$

The $ED_{50}$ does, ie. the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J Pharmacol. Exp. Ther., 96 99–113, (1949).

The results of these tests are set out in the following Table I.

TABLE I

| ISOQUINOLINE PROPIONAMIDES ANALGESIC DATA | | | | | | | | | | |
|---|---|---|---|---|---|---|---|---|---|---|
| Compound | Example No. | R | R' | X | A | pY | q | n | $ED_{50}$ (mg/kg) | 95% Confidence Limits |
| TR-3284 | 1 | $CH_3$ | H | H | CH | HCl | 0 | 0 | 7.10 | (3.64–13.9) |
| TR-3207 | 2 | $CH_2-$ | H | H | CH | HCl | 0 | 0 | 7.45 | (2.68–20.7) |
| TR-3309 | 3 | $(CH_2)_5CH_3$ | H | H | CH | $C_2H_2O_4$ | 1 | 0 | 2.08 | (1.33–3.25) |
| TR-3316 | 4 | $(CH_2)_4CH_3$ | H | H | CH | HCl | 0 | 0 | 1.76 | (0.90–3.43) |
| TR-3280 | 5 | $(CH_2)_2C_6H_5$ | H | H | CH | HCl | 0 | 0 | 10.0* | (5.7–17.5) |
| TR-3317 | 6 | $(CH_2)_2CH(CH_3)_2$ | H | H | CH | HCl | 0 | 0 | 16.5* | (7.9–34.7) |
| TR-3354 | 7 | $CH_3$ | H | Cl | CH | HCl | 0 | 0 | 0.50 | (0.09–2.65) |
| TR-3355 | 8 | $CH_3$ | H | $CH_3$ | CH | HCl | 0 | 0 | 0.53 | (0.27–1.06) |
| TR-3359 | 9 | $Ch_2C_6H_5$ | H | H | CH | HCl | 0 | 0 | 15.0 | (6.7–33.8) |
| TR-3389 | 10 | $CH_3$ | H | H | CH | $C_2H_2O_4$ | 0 | 1 | 23.0 | (4.4–119) |
| TR-3388 | 11 | $CH_2C_6H_5$ | H | H | CH | $C_2H_2O_4$ | 0 | 1 | 33.0 | (6.5–168) |
| TR-3426 | 12 | $CH_3$ | $OCH_3$ | H | CH | 0 | 0 | 0 | 4.55 | (0.70–29.6) |
| TR-3461 | 13 | $CH_3$ | H | H | N | HCl | 0 | 0 | 10.7 | (4.4–26.1) |

*According to IMTE writhing test protocol

Compounds of this invention may be prepared and utilized in the form of the free base. Preferably, however, the compounds are used as pharmacologically acceptable, non-toxic, water soluble addition salts of acids such as halogen acids, sulfuric acid, maleic acid and oxalic acid.

These compounds, either in the form of the free base or acceptable addition salts, are useful as analgesic agents. Medications prepared with these compounds as active ingredients are readily formulated by mixing the compounds in dosage units with fillers, carriers, extenders and/or excipients generally used in preparing pharmaceutical formulations. When mixed in such formulations the compound may be in the form of the free base but is preferably in the form of a pharmacologically acceptable addition salt. The medication may be either in solid or liquid form and may be compounded as tablets, powders, capsules, suspensions and similar dosage forms according to accepted manufacturing methods.

These medications may be administered, for example, orally or subcutaneously in conformity with recognized pharmacological techniques.

What is claimed is:

1. N-[(1,2,3,4-Tetrahydro-2-methyl-1-isoquinolyl)methyl]N-(4-chlorophenyl)propionamide having the structural formula:

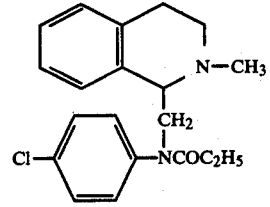

2. The compound of claim 1 in the form of its hydrochloric acid addition salt.

* * * * *